United States Patent
Kim et al.

(10) Patent No.: US 11,027,741 B2
(45) Date of Patent: Jun. 8, 2021

(54) APPARATUS AND METHOD FOR ESTIMATING DRIVER READINESS AND METHOD AND SYSTEM FOR ASSISTING DRIVER

(71) Applicant: ELECTRONICS AND TELECOMMUNICATIONS RESEARCH INSTITUTE, Daejeon (KR)

(72) Inventors: Hyun Suk Kim, Daejeon (KR); Dae Sub Yoon, Daejeon (KR); Woo Jin Kim, Daejeon (KR); Seung Jun Lee, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 344 days.

(21) Appl. No.: 16/184,163

(22) Filed: Nov. 8, 2018

(65) Prior Publication Data

US 2019/0143990 A1    May 16, 2019

(30) Foreign Application Priority Data

Nov. 15, 2017 (KR) ......................... 10-2017-0152570
Oct. 8, 2018 (KR) ......................... 10-2018-0120004

(51) Int. Cl.
*A61B 5/18* (2006.01)
*B60W 40/08* (2012.01)
(Continued)

(52) U.S. Cl.
CPC ........... *B60W 40/08* (2013.01); *G05D 1/0061* (2013.01); *G05D 1/0088* (2013.01); *G06N 7/005* (2013.01);
(Continued)

(58) Field of Classification Search
CPC .......... A61B 5/163; A61B 5/18; B60W 40/08; B60W 50/10; B60W 2540/22;
(Continued)

(56) References Cited

U.S. PATENT DOCUMENTS 8,515,610 B2    8/2013  Sung et al.
9,690,292 B1*   6/2017  Chan .................... B60W 40/09
(Continued)

FOREIGN PATENT DOCUMENTS

JP     2017-019424 A     1/2017
KR   10-2014-0076910 A   6/2014
(Continued)

*Primary Examiner* — Anshul Sood
(74) *Attorney, Agent, or Firm* — LRK Patent Law Firm

(57) ABSTRACT

A method of estimating driver readiness in a vehicle for performing automated driving includes analyzing a bio-signal and a behavior of a driver through collected driver information, determining a bodily sensory usage state of the driver from the behavior of the driver, deriving chances of task candidates that are probable to occur from the driver during driving from the bodily sensory usage state of the driver to infer a task, determining an intention of the driver on the basis of the inferred chances of the task candidates, and calculating driver readiness using the intention of the driver.

18 Claims, 7 Drawing Sheets

(51) Int. Cl.
*G05D 1/00* (2006.01)
*G06N 7/00* (2006.01)

(52) U.S. Cl.
CPC ............ *A61B 5/18* (2013.01); *B60W 2540/22* (2013.01); *G05D 2201/0213* (2013.01)

(58) Field of Classification Search
CPC ............... G05D 1/0061; G05D 1/0088; G05D 2201/0213; G06N 7/005
See application file for complete search history.

(56) References Cited

U.S. PATENT DOCUMENTS

| | | | |
|---|---|---|---|
| 2011/0040540 A1* | 2/2011 | Yoon ...................... | G06Q 10/06 703/6 |
| 2017/0192436 A1 | 7/2017 | Min et al. | |
| 2017/0249844 A1* | 8/2017 | Perkins ................. | B60W 40/00 |
| 2017/0282930 A1* | 10/2017 | Kochhar ................ | B60W 50/10 |
| 2017/0355377 A1* | 12/2017 | Vijaya Kumar .. | B60W 50/0098 |
| 2017/0364070 A1 | 12/2017 | Oba | |
| 2018/0032072 A1* | 2/2018 | Hoye .................... | B60W 40/08 |
| 2018/0053108 A1* | 2/2018 | Olabiyi ................. | B60W 40/09 |

FOREIGN PATENT DOCUMENTS

| | | |
|---|---|---|
| KR | 10-1659034 B1 | 9/2016 |
| KR | 10-2017-0107373 A | 9/2017 |

\* cited by examiner

FIG. 4

| Task Candidates | Workload Details | | | | Total Workload |
|---|---|---|---|---|---|
| | Visual | Auditory | Cognition | Psychomotor | |
| No Task | Low | Low | Low | Low | $W_{no\_task}$ |
| Texting | Low | Low | Middle | Middle | $W_{texting}$ |
| Watching Movie | Middle | Middle | Middle | Low | $W_{movie}$ |
| Eating/Drinking | Low | Low | Low | Middle | $W_{eating}$ |
| Talking/Conversation | Low | High | High | Low | $W_{talking}$ |

APPARATUS AND METHOD FOR ESTIMATING DRIVER READINESS AND METHOD AND SYSTEM FOR ASSISTING DRIVER

CROSS REFERENCE TO RELATED APPLICATIONS

This application claims priority to Korean Patent Application No. 10-2017-0152570, filed Nov. 15, 2017, and Korean Patent Application No. 10-2018-0120004, filed Oct. 8, 2018, in the Korean Intellectual Property Office (KIPO), the entire contents of which are hereby incorporated by reference.

BACKGROUND

1. Technical Field

Example embodiments of the present invention relate in general to the field of an apparatus and method for estimating driver readiness and a method and system for assisting a driver, and more specifically to an apparatus and method for estimating a driver readiness required for switching into a manual driving mode in a vehicle capable of performing automated driving and a method and system for assisting a driver relevant to the apparatus and method for estimating the driver readiness.

2. Description of Related Art

The yearly number of deaths from vehicle accidents worldwide amounts to 1.24 million (4,762 in Korea, 2014), 90% of which are attributed to driver's faults, such as taking eyes off the road, drowsy driving, and the like (The World Health Organization (WHO), 2012).

In this regard, as a conventional technology for assisting the driver in driving a vehicle, there has been suggested a technology in which a state of inability to drive is determined by analyzing a preset basic monitoring area in image information of a human driver captured during manual driving and monitoring a lane departure with reference to driving state monitoring information, and a preset alarm is indicated to the driver. In addition, there has been suggested a technology in which the posture of the driver is estimated, and the blinking rate, the percentage of eyes being closed, and the head movement are measured using a camera included in a vehicle, and biometric data is acquired using a sensor wearable by a driver, to measure the degree of drowsiness of the driver and assist the driver to stay awake, thereby interacting with the driver of the vehicle according to situations during manual driving.

Meanwhile, as a way to remarkably reduce traffic accidents caused by the driver's faults, automated vehicles are actively studied. Developed countries, such as the United States, Japan, and Europe, and automobile companies spur the development of automated vehicle technology. The automated driving technology is expected to make remarkable contribution to the reduction of traffic congestion through traffic control as well as the reduction of traffic accidents by improving the driving safety.

In this regard, there is a need for a detailed methodology for dealing with a state of a driver's inability to drive, which occurs from sleepiness, fatigue, and unexpected physical conditions of a driver during automated driving rather than manual driving.

SUMMARY

Accordingly, example embodiments of the present invention are provided to substantially obviate one or more problems due to limitations and disadvantages of the related art.

Example embodiments of the present invention provide a method of estimating driver readiness that is required for switching into a manual driving mode in a vehicle capable of performing automated driving.

Example embodiments of the present invention also provide an apparatus for estimating driver readiness using the method of estimating driver readiness.

Example embodiments of the present invention also provide a method of assisting a driver in a vehicle capable of performing automated driving.

In some example embodiments, a method of estimating driver readiness in a vehicle capable of performing automated driving includes: analyzing a bio-signal and a behavior of a driver through collected driver information; determining a bodily sensory usage state of the driver from the behavior of the driver, deriving chances of task candidates that are probable to occur from the driver during driving from the bodily sensory usage state of the driver to infer a task; determining an intention of the driver on the basis of the inferred chances of the task candidates; and calculating driver readiness using the intention of the driver.

The bodily sensory usage state of the driver may include usage states of a visual sense (V), an auditory sense (A), a cognitive sense (C), and a psychomotor sense (P).

The chances of the task candidates may include a posterior probability value for each task candidate calculated using at least one of a bodily sensory usage state of each task candidate and a situation awareness state of the driver.

The deriving of the chances of task candidates that are probable to occur during driving from the bodily sensory usage state of the driver may include acquiring bodily sensory usage state information of at least one task candidate from a task model in which bodily sensory usage level information of at least one task is accumulated and stored; and calculating a global posterior probability of the task using the bodily sensory usage state of the at least one task candidate as a prior probability.

The determining of the intention of the driver on the basis of the inferred chances of the task candidates may include determining the intention of the driver from a task inferred using an accumulated task inference history.

The calculating of the driver readiness using the intention of the driver may include calculating the driver readiness by considering at least one of the intention of the driver and a total workload of the driver.

The method may further include: collecting biometric information of the driver and identifying a health status of the driver by analyzing the bio-information of the driver.

The calculating of the driver readiness using the intention of the driver may include calculating the driver readiness by further considering a health status of the driver and reaction time information for take over request (TOR).

In other example embodiments, an apparatus for estimating driver readiness in a vehicle capable of performing automated driving includes a processor, and a memory configured to store at least one command executed through the processor, wherein the at least one command includes: a command for analyzing a bio-signal and a behavior of a driver through collected driver information; a command for determining a bodily sensory usage state of the driver from the behavior of the driver, a command for inferring a task by deriving chances of task candidates that are probable to occur from the driver during drive from the bodily sensory usage state of the driver, a command for determining an intention of the driver on the basis of the inferred chances of the task candidates; and a command for calculating driver readiness using the intention of the driver.

The bodily sensory usage state of the driver may include usage states of a visual sense (V), an auditory sense (A), a cognitive sense (C), and a psychomotor sense (P).

The chances of the task candidates may include a posterior probability value for each task candidate calculated using at least one of a bodily sensory usage state of each task candidate and a situation awareness state of the driver.

The command for inferring the task may include: a command for acquiring bodily sensory usage state information of at least one task candidate from a task model in which bodily sensory usage level information of at least one task is accumulated and stored; and a command for calculating a global posterior probability for the task by using the bodily sensory usage state information of the at least one task candidate as a prior probability.

The command for determining the intention of the driver may include a command for determining an intention of the driver from a task inferred using an accumulated task inference history.

The command for calculating the driver readiness using the intention of the driver may include a command for calculating the driver readiness by considering at least one of the intention of the driver and a total workload of the driver.

The at least one command may further include a command for collecting bio-information of the driver and a command for identifying a health status of the driver by analyzing the bio-information of the driver.

In still other example embodiments, a method of assisting a driver in a vehicle capable of performing automated driving includes: deriving chances of task candidates that are probable to occur from the driver during driving from a bodily sensory usage state of the driver to infer a task; calculating driver readiness on the basis of the chances of the task candidates; determining whether the driver readiness is higher than or equal to a readiness threshold; and operating at least one driver interaction device on the basis of the driver readiness in consideration of at least one of a driving environment, a driving route, vehicle information, and a health status of the driver.

The bodily sensory usage state of the driver may include usage states of a visual sense (V), an auditory sense (A), a cognitive sense (C), and a psychomotor sense (P).

The chances of the task candidates may include a posterior probability value for each task candidate calculated using at least one of a bodily sensory usage state of each task candidate and a situation awareness state of the driver.

The calculating of the driver readiness on the basis of the chances of the task candidates may include: determining an intention of the driver from a task inferred using an accumulated task inference history; and calculating the driver readiness by considering at least one of the intention of the driver and a total workload of the driver.

BRIEF DESCRIPTION OF DRAWINGS

Example embodiments of the present invention will become more apparent by describing example embodiments of the present invention in detail with reference to the accompanying drawings, in which:

FIG. 4 is a diagram illustrating the degrees to which bodily senses are used for each task candidate according to an embodiment of the present invention;

DETAILED DESCRIPTION OF EXAMPLE EMBODIMENTS

Figure 1:
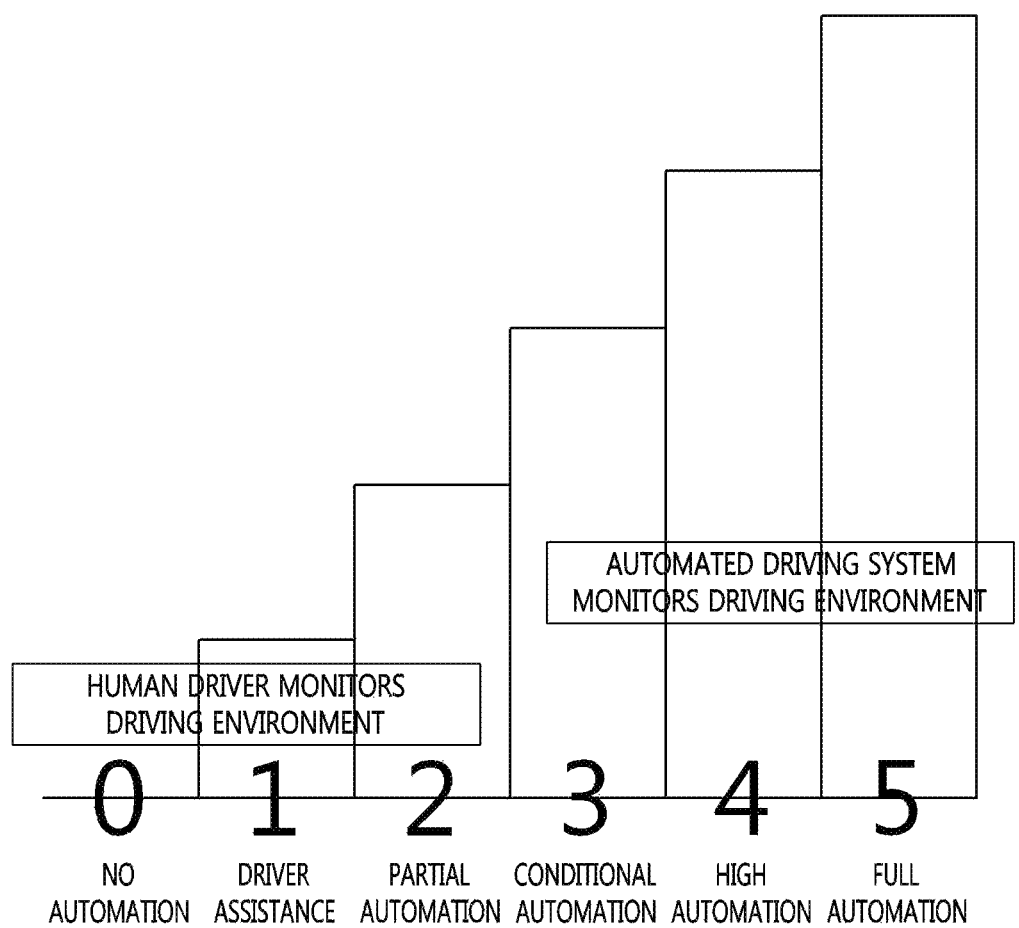
FIG. 1 is a diagram illustrating the concept of six levels of driving automation according to Society of Automotive Engineers (SAE) J3016.

While the present invention is susceptible to various modifications and alternative embodiments, specific embodiments thereof are shown by way of example in the drawings and will be described in detail. However, it should be understood that there is no intention to limit the present invention to the particular forms disclosed, rather the present invention is to cover all modifications, equivalents, and alternatives falling within the spirit and scope of the present invention. Like numbers refer to like elements throughout the description of the drawings.

It will be understood that, although the terms first, second, A, B, etc. may be used herein to describe various elements, the elements should not be limited to the terms. The terms are only used to distinguish one element from another. For example, a first element could be termed a second element, and, similarly, a second element could be termed a first element, without departing from the scope of the present invention. As used herein, the term "and/or" includes any one or combinations of the associated listed items or any item of one or more of the associated listed items.

It will be understood that when an element is referred to as being "connected" or "coupled" to another element, it can be directly connected or coupled to another element or intervening elements may be present. In contrast, when an element is referred to as being "directly connected" or "directly coupled" to another element, there are no intervening elements present.

The terminology used herein is for the purpose of describing particular embodiments only and is not intended to be limiting of the present invention. As used herein, the singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms including technical and scientific terms and used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described with reference to the accompanying drawings in detail.

FIG. 1 is a diagram illustrating the concept of six-level automation of driving according to Society of Automotive Engineers (SAE) J3016.

With the goal of providing common terminology for automated driving, SAE International's standard J3016, under the heading "Taxonomy and Definitions for Terms Related to On-Road Motor Vehicle Automated Driving Systems" defines six levels of driving automation from "no automation" to "full automation" as shown in FIG. 1, specifies base definitions and levels on functional aspects of technology, and describes categorical distinctions for a stepwise progression through the levels. The definitions are consistent with current industry practice, eliminate confusion and are useful across numerous disciplines (engineering, legal, media, and public discourse), and also clarify for each level what role (if any) drivers have in performing a dynamic driving task while a driving automation system is engaged. Here, SAE stands for Society of Automotive Engineers.

Here, the dynamic driving task includes the operational (driving, steering, braking, accelerating, and monitoring of the vehicle and roadway) and tactical (responding to events, determining when to change lanes, turn, use signals, and the like) aspects of the driving task, but not the strategic (determining destinations and waypoints) aspect of the driving task.

As to review the levels of driving automation defined in SAE J3016 in more detail, level 0 is a "No Automation" level, in which steering, acceleration, deceleration, and the like are performed by a human driver, and not only monitoring of the driving environment but also fallback performance of the dynamic driving task is performed by a human driver.

Level 1 is defined as a "Driver Assistance" level, Level 2 is defined as a "Partial Automation" level, Level 3 is defined as a "Conditional Automation" level, and Level 4 is defined as a "High Automation" level. Level 5 is defined as a "Full Automation" level, i.e., a stage in which fully automated driving is achieved, and therefore not only the driving tasks, such as steering, accelerating, decelerating, and the like, but also the monitoring of driving environment and the fallback performance of dynamic driving task are performed by an automated system.

Referring to FIG. 1, a key distinction in the driving automation is a point between Level 2 and Level 3. This is because a dynamic driving task is performed by a human driver until Level 2, and the entire dynamic driving task is performed by the automated driving system from Level 3. In other words, in Levels 0, 1, and 2, monitoring the driving environment is performed by the human driver, but in Levels 3, 4, and 5, monitoring the driving environment is performed by the automated system.

To summarize, the role of a driver in an automated driving situation is varied according to the step of automated driving. Until Level 3, the importance on the role of the driver is stressed, and in Level 4 or higher, the intervention of the driver decreases to almost none. In a manual mode, the driver is engaged in most driving tasks, and driving tasks for an automated driving situation are performed by an automated driving system (ADS) installed in the vehicle. However, when the ADS fails in the automated driving mode, the driver needs to take over control and perform driving.

In addition, when switching between the SAE Level 2 and the SAE Level 3, which is the key distinction in the six levels as described above, a stable transfer of the control between the driver and the vehicle is an important issue. When an error occurs in the control transfer process, a gap is generated in the control of the vehicle and thus an accident may occur. When the control is transferred from the driver to the vehicle, the automated driving mode is immediately activated and thus the possibility of having an accident is low. However, when the control is transferred from the vehicle to the driver, the reaction speed may be slow due to the attention dispersion of the driver (for example, the attention dispersion occurs since the driver has a chance to perform a non-driving related task during automated driving), thus leading to an accident. Accordingly, there is a need for a technology for evaluating and determining a state of readiness in which a driver is able to take over control and drive.

The present invention suggests a method of determining and analyzing whether a driver is able to take over control and manually drive when an automated vehicle desires to transfer a drive control from an automated driving based on an automatic driving system to manual driving, and a DRE system using the method.

The present invention provides a system for observing a driver and maintaining driver readiness to be higher than or equal to a threshold rather than monitoring a state of the driver dozing or unable to drive in manual driving, to provide an environment enabling the driver to drive at any time while an automated driving is proceeding in an automated vehicle.

In addition, the present invention provides a system capable of detecting various behaviors of a driver related to a driving inhibition factor, such as rest/sleeping, texting, video watching, eating/drinking, talking and the like, and capable of predicting a point at which manual driving is imminent in consideration of the surrounding road condition and the driving situation and adjusting the driver readiness for manual driving to be higher than or equal to a threshold on the basis of the predicted point, without unconditionally waking up the driver and allowing the driver to be prepared for driving.

Figure 2:
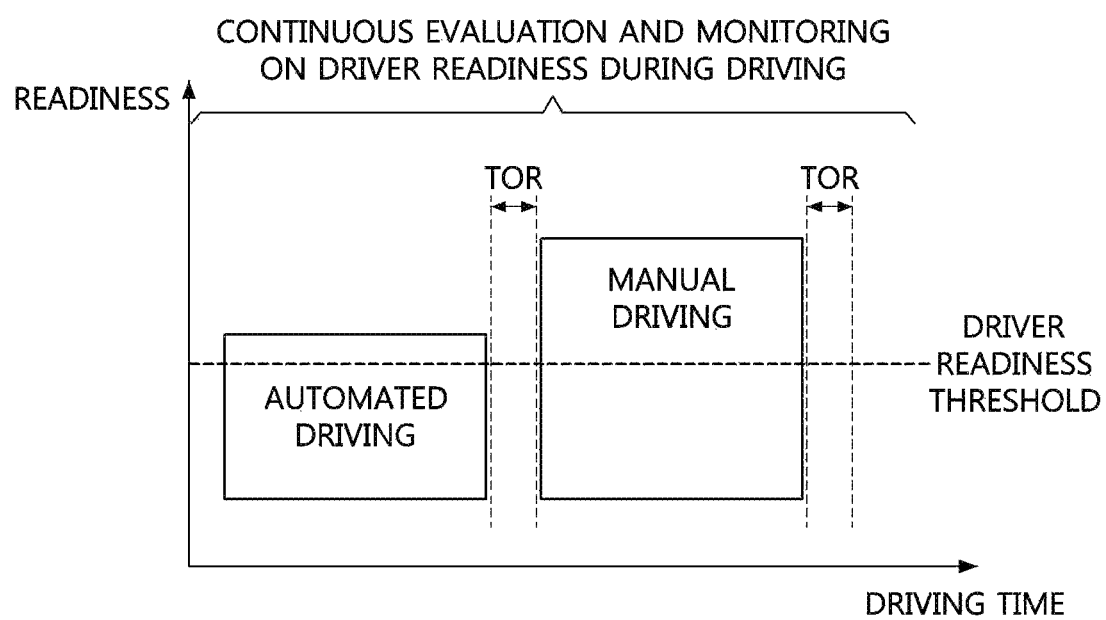
FIG. 2 is a diagram showing the relationship between automated and manual driving and driver readiness in automated driving according to an embodiment of the present invention.

FIG. 2 is a diagram showing the relationship between automated and manual driving and driver readiness in automated driving according to an embodiment of the present invention.

In an automated vehicle with the SAE Level 2 and the SAE Level 3, control is transferred from the driver to the vehicle, the automated driving mode is immediately activated and thus the possibility of having an accident is low. However, when the control is transferred from the vehicle to the driver, the reaction speed may be slow due to the attention dispersion of the driver, leading to an accident. Accordingly, there is a need for a technology for evaluating and determining a state of readiness in which a driver is able to take over the control and drive.

Accordingly, the present invention proposes a DRE (Driver Readiness Estimator) system capable of determining and analyzing driver readiness, which is a driver's ready state of vehicle operation. At this time, the driver readiness is analyzed after synchronizing the behavior information, health status information, surrounding driving environment information and vehicle driving information which is analyzed and extracted using a sensing device installed in the vehicle.

Referring to FIG. 2, the driver readiness is a concept of quantifying whether a driver is ready to take over a driving control and manually drive when there is a need to switch into manual driving in an automated driving situation of an automated vehicle. For example, when a driver is tedious or is fully distracted by a secondary task, the driver readiness indicates a low level, and the driver has a high risk of failing to stably drive upon requesting a transfer for manual driving.

Accordingly, the driver may be required to maintain readiness higher than or equal to a certain driver readiness threshold such that manual driving is performed at any time during automated driving. Here, TOR stands for Take Over Request.

Figure 3:
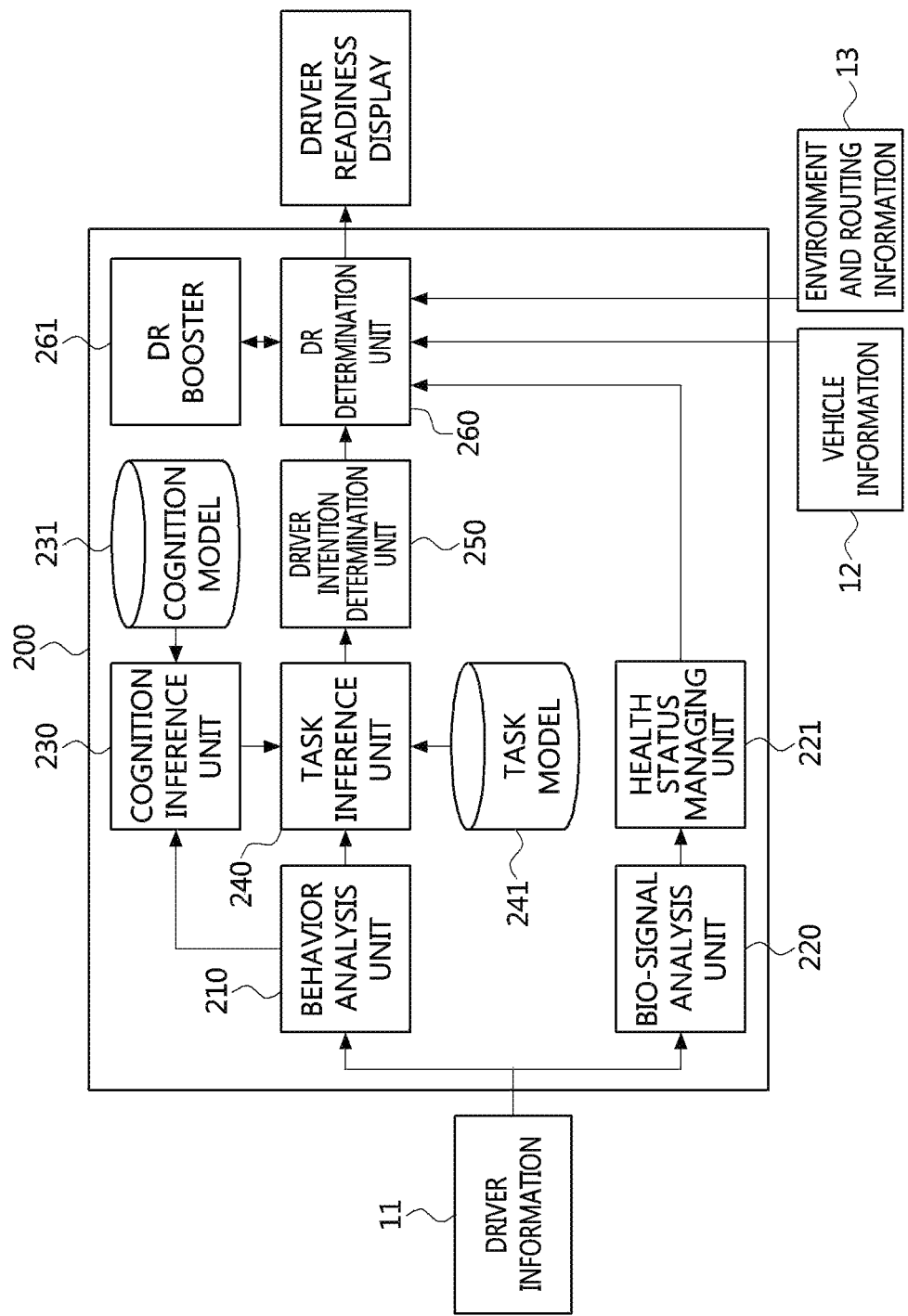
FIG. 3 is a block diagram illustrating a Driver Readiness Estimator (DRE) apparatus according to an embodiment of the present invention.

FIG. 3 is a block diagram illustrating a DRE apparatus according to an embodiment of the present invention.

Referring to FIG. 3, a DRE system of an automated vehicle may monitor behaviors of the driver except for driving tasks during automated driving.

The DRE apparatus 200 may identify a cognition state of the driver through a behavior inference of a driver using driver information 11, vehicle information 12, and environment and routing information 13, so that a driver readiness value having a high reliability is derived.

The driver information 11 may be collected using sensors installed in the vehicle and may be utilized for analyzing the behavior of the driver. That is, a behavior analysis unit 210 analyzes information related to the behavior of the driver among pieces of collected information. In order to analyze the behavior of the driver, the DRE apparatus 200 may include a sensor, a module or a device having a body motion sensing function, a sensor, a module or a device having an eye tracking function, and a sensor, a module or a device having a head movement sensing function, or may operate in conjunction with such devices installed in the vehicle.

In addition, bio-information of the driver among the pieces of driver information may be utilized to analyze the health status of the driver. A bio-signal analysis unit 220 collects and analyzes bio-information of the driver among the pieces of driver information and transmits the collected and analyzed bio-information to a health status managing unit 221 for the driver, and the health status managing unit 221 performs time synchronization with respect to pieces of data analyzed by the bio-signal analysis unit 220, compares the data with a health-related reference value and the like, to thereby comprehensively determine the health status of the driver and perform an integrated management of the health status of the driver. A sensor, a module or a device for collecting bio-signals to analyze the health status of the driver may be installed in the vehicle. Here, the bio-signal may include electroencephalogram (EEG), electrocardiogram (ECG), galvanic skin response (GSR), photoelectric pulse diagram (PPG), skin temperature (SKT), respiration rate, and the like.

Driver behaviors that a driver may have in an automated driving mode of a vehicle during automated driving include various behaviors, such as resting/sleeping, texting, video watching, eating/drinking, talking with an occupant, and the like.

The behavior analysis unit 210 detects such driver behavior information and transmits the detected driver behavior information to a cognition inference unit 230.

The cognition inference unit 230 extracts cognition information according to a behavior. In more detail, the cognition inference unit 230 may determine a bodily sensory usage state of the driver according to a driver behavior using a cognition model 231 that is accumulated in advance. The bodily sensory usage state includes a usage level (a usage state) of a visual sense V, an auditory sense A, a cognitive sense C, and a psychomotor sense P. For example, between the talking with an occupant and the texting, the usage level of V-A-C-P, which is an output value of the cognition inference unit 230, may be determined to be different according to the characteristics of each behavior.

A cognition inference result, which is the output value of the cognition inference unit 230, may be input to a task inference unit 240. The task inference unit 240 may calculate chances of task candidates that the driver may have during automated driving, on the basis of the cognition inference result input from the cognition inference unit 230, that is, the usage level of V-A-C-P.

In this case, a situation awareness (SA) performed to identify the degree to which the driver identifies the driving situation may also be included in the task candidate. In other words, a state of the situation awareness of the driver is a value indicating the degree to which the driver identifies the driving environment (information about an accident in the front of the vehicle or information about a construction section), the driving route, and the remaining distance and time during automated driving.

The task inference unit 240 may additionally use V-A-C-P distributions according to task candidates which are accumulated in the task model 241. For example, a V-A-C-P distribution of task 1 may be expressed using probabilities p(v|T1), p(a|T1), p(c|T1), and p(p|T1) for the visual, auditory, cognitive, and psychomotor factor. Here, T1 may denote Task 1.

In order to calculate the chances of the task candidates, the V-A-C-P distribution of each task is set as a prior probability, and a global posterior probability is calculated. A chance (P (T|v, a, c, p)) of Task with respect to the current V-A-C-P value, that is, a posterior probability $p_T$ may be expressed by Equation 1 below.

$$p_T = \\ P(T \mid v, a, c, p) = \frac{q_T\, p(T)}{\{qSA\ p(SA) + \ldots + qRead\ p(Read) + qOthers\ p(Others)\}}$$

[Equation 1]

$$q_T = p(v, a, c, p \mid T)$$

$$q_{Others} = \prod_{j \in T'_s} (1 - q_j)$$

$$p(v, a, c, p \mid T) = p(v \mid T)p(a \mid T)p(c \mid T)p(p \mid T)$$

In Equation 1, $p_T$ is a posterior probability, p (T) is a prior probability that Task T may occur, and is expressed as p (SA), p (Read), p (Others), and the like in Equation 1. $q_T$ refers to a probability of occurrence for v, a, c, and p in the case of performing Task T, that is, a likelihood, and is represented as p (v, a, c, p|T). In addition, the likelihood, that is, p (v, a, c, p|T) may be acquired from the task model 241.

The usage level of V-A-C-P of the driver and the chance of the task (the probability), which are calculated by the task inference unit 240, may be transmitted to a driver intention determination unit 250.

When the task inference unit 240 infers the task of the driver from a measurement value of the current point of time, the driver intention determination unit 250 determines the intention of the driver from an accumulated task inference history. The driver intention determination unit 250 may not determine that the driver is in a sleeping state even when the V-A-C-P of the driver is temporarily lowered, but determine the state of the driver by referring to the history information.

For example, when the intention of a task, referred to as SA, is determined, the intention $p_{DI}$ of the SA task of the driver is determined as shown in Equation 2 below.

$$p_{DI} = p(SA = 1 \mid p_1, p_2, p_3) \quad \text{[Equation 2]}$$
$$= \frac{P(p_1, p_2, p_3 \mid SA = 1)P(SA = 1)}{P(p_1, p_2, p_3 \mid SA = 1)P(SA = 1) + P(p_1, p_2, p_3 \mid SA = 0)P(SA = 0)}$$
$$= \prod_j p_j + \prod_j (1 - p_j)$$
$$= \frac{\prod_j p_j}{\prod_j p_j + \prod_j (1 - p_j)}$$
$$= \left(1 + \prod_j \left(\frac{1}{p_j} - 1\right)\right)^{-1}$$

In Equation 2, $P_j$ may denote history information accumulated up to the current point of time, and the influence of $P_j$ may decrease over time. Meanwhile, Equation 2 is described by taking the SA task as an example, but the same method as shown in Equation 2 may apply to another task.

Here, $P_j$ may be expressed by Equation 3.

$$p_j = 0.5 + (p_{SA}(t-j) - 0.5)e^{-\alpha j} \quad \text{[Equation 3]}$$

In Equation 3, α denotes a forgetting factor.

The driver intention and the V-A-C-P usage level about the SA task calculated by the driver intention determination unit 250 may be transmitted to a DR determination unit 260.

The final driver readiness may be calculated using the driver intention of the task performed by the driver and the usage level of V-A-C-P of the driver. A driver readiness $DR_t$ at a specific time t may be determined, for example, according to Equation 4 below.

$$DR_t = 100 - \{W_t\} \quad \text{[Equation 4]}$$

In Equation 4, Wt denotes the total workload of the driver, and may be defined, for example, as Equation 5 below.

$$W_t = (a_t{}^*V) + (b_t{}^*A) + (c_t{}^*C) + (d_t{}^*P) \quad \text{[Equation 5]}$$

Here, $a_t$, $b_t$, $c_t$, and $d_t$ are weighting factors of each of V, A, C, and P of the driver, and t is a time index. The weighting factor for each of V, A, C, and P may be varied according to the determined intention of the driver as shown in FIG. 4.

FIG. 4 is a diagram illustrating the degrees to which bodily senses are used for each task candidate according to an embodiment of the present invention.

Referring to FIG. 4, in the case of a texting task, the usage levels of a cognitive sense and a psychomotor sense have middle values, in the case of eating/drinking, the usage level of a psychomotor sense has a middle value, and in the case of talking, the usage levels of an auditory sense and a cognitive sense have high values. In other words, the weight of each bodily sense is differently set according to the intention of the driver, that is, the task being performed.

To summarize, the total workload of the driver may be calculated using the usage level of V-A-C-P of the driver and the weight according to the intention of the driver. In addition, as can be seen from Equation 4, the driver readiness may decrease as the total workload of the driver increases, with an inverse relationship.

Although the above-described embodiments have been described in relation to the process of inferring the driver readiness through the driver V-A-C-P, the scope of the present invention is not limited to the above-described specific methods, and may include other behaviors or bio-information of the driver in addition to V-A-C-P.

The bio-information of the driver may be continuously measured using the sensors in the vehicle starting from the moment at which the driver rides on the vehicle, and be transmitted to the bio-signal analysis unit 220. Information about bio-signals (EEG, ECG, GSR, PPG, SKT, and respiration rate) measured from various sensors may be analyzed for each bio-signal, and the analyzed information may be transmitted to the health status managing unit 221. The health status managing unit 221 may aggregate all the pieces of analyzed bio-signal information and transmit a health status, such as a respiratory state, stress, fatigue, and the like, to the DR determination unit 260.

The DR determination unit 260 may determine the driver readiness by aggregating the V-A-C-P availability and the TOR reaction time information which are input from the driver intention determination unit 250, driver health status information which is input from the health status managing unit 221, and vehicle speed information and road driving environment information among vehicle information so as to determine a state of able to drive.

During automated driving, the role of a driver may be varied according to the steps of automated driving. Until Level 3, the importance on the role of the driver is stressed, and in Level 4 or higher, an intervention of the driver does not exist. Accordingly, an automated vehicle driving between the SAE Level 2 and the SAE Level 3 may be subject to a transfer of a driving control from an automated driving mode to a manual driving mode at any time.

The automatic driving system according to the embodiment of the present invention periodically monitors whether the driver readiness information determined by the DR determination unit 260 falls to be lower than the threshold, and in that case, notifies a DR booster 261 that the driver readiness information falls to be lower than the threshold.

The DR booster 261 may operate at least one driver interaction device to increase the driver readiness. Here, the driver interaction device is an operation device related to visual, auditory, and tactile senses, and may contribute to enhancing the driver readiness by controlling an active interaction with the driver. Examples of the user interaction device may include a seat belt operation, a warning alarm, and the like, and the DR booster 261 may be provided using a device capable of refreshing the driver's visual, auditory, and tactile senses in various ways according to the situation of the driver.

The driving ability and health status of individual drivers may vary from person to person, and thus in an implementation, the above-described driver readiness may be continuously tuned to a system optimized for the driver.

In addition, the DR determination unit 260 may comprehensively identify the vehicle information 12 and the environment and routing information 13, and suppress the activation of the user interaction device caused by the DR booster 261. In other words, the DR determination unit 260 identifies a driving route, a surrounding driving environment, and the like that are set by a navigation system, and for example, when an automated driving for highway is expected to take 30 minutes or longer to a destination, the DR determination unit 260 may suppress the operation of the DR booster such that the driver is allowed to have a short rest or to doze even when the driver readiness is lower than or equal to the threshold.

Figure 5:
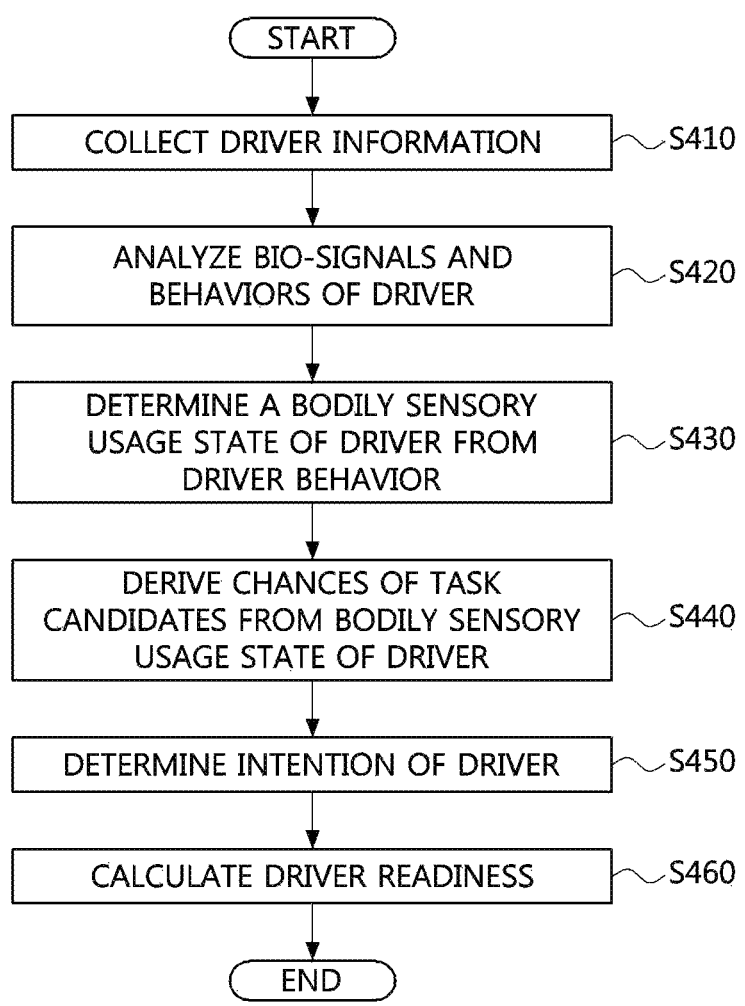
FIG. 5 is an operation flowchart showing a method of estimating driver readiness according to an embodiment of the present invention.

FIG. 5 is an operation flowchart showing a method of estimating driver readiness according to an embodiment of the present invention.

Referring to FIG. 5, the method of estimating driver readiness according to the embodiment of the present invention first includes collecting driver information (S410) and analyzing bio-signals and behaviors of the driver through the collected driver information (S420). The behavior of the driver is used to determine a bodily sensory usage state of the driver (S430). The bodily sensory usage state of the driver may include a usage state of a visual sense V, an auditory sense A, a cognitive sense C, and a psychomotor sense P of the driver. When determining the bodily sensory usage state of the driver, a cognition model may be further used.

When the bodily sensory usage state of the driver is determined, chances of task candidates that are probable to occur from the driver during drive are derived to infer a task (S440). Here, the chances of the task candidates may include a posterior probability value for each task candidate that is calculated using the bodily sensory usage state of each task candidate. In the task model, bodily sensory usage level information of at least one task is accumulated and stored. Specifically, in order to infer a task, bodily sensory use state information for at least one task candidate is obtained from the task model, and the global posterior probability for the task is calculated by using it as a prior probability.

In addition, the intention of the driver is determined on the basis of the inferred chances of the task candidates (S450). The intention of the driver may be determined from a task inferred using an accumulated task inference history.

When the intention of the driver is determined, the driver readiness is calculated using the determined intention of the driver (S460). As will be described below, a method of assisting a driver according to an embodiment drives the user interaction device according to the driver readiness to assist in maintaining the driver readiness at a certain threshold or higher.

Figure 6:
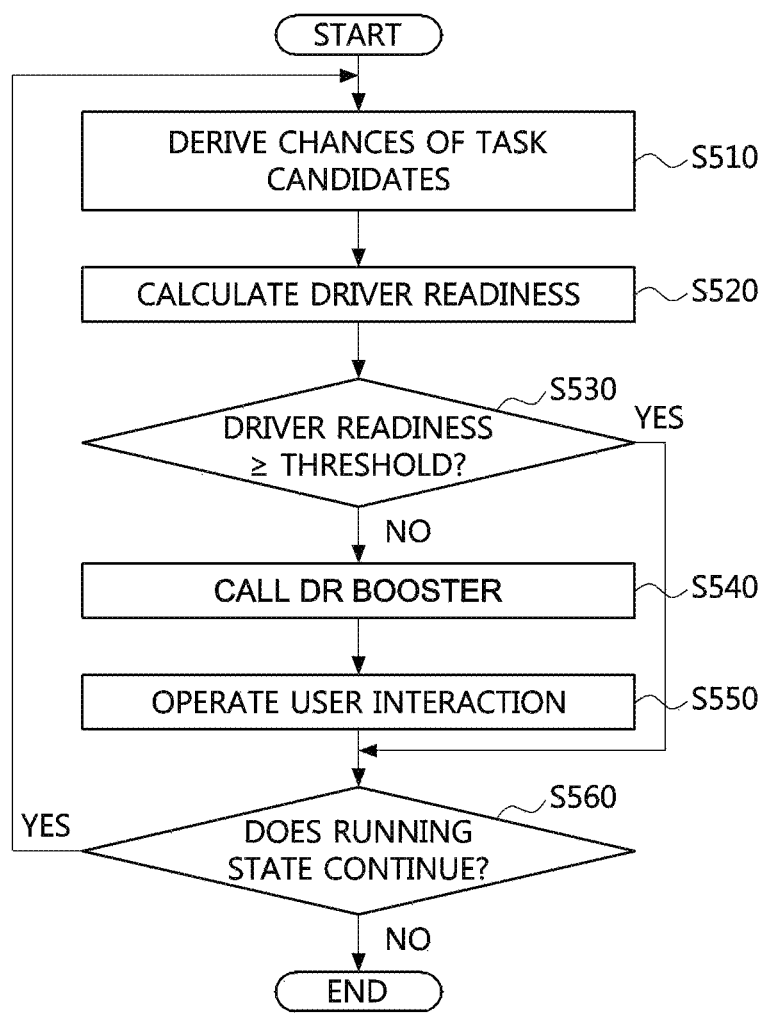
FIG. 6 is an operation flowchart showing a method of assisting a driver according to an embodiment of the present invention.

FIG. 6 is an operation flowchart showing a method of assisting a driver according to an embodiment of the present invention. The method of assisting a driver according to the embodiment of the present invention shown in FIG. 6 relates to a method of assisting a driver at a time of switching into manual driving in a vehicle capable of performing automated driving.

Referring to FIG. 6, when an automated vehicle starts to run, the DRE system according to the present invention operates to derive the chances of task candidates (S510) and calculate driver readiness (S520).

The calculated driver readiness is compared with a threshold (S530). When the driver readiness is less than the threshold in which the driver is able to take over control and drive (NO in S530), the DR booster is called to increase the driver readiness (S540). The DR booster operates the interaction device differently in each case of the V-A-C-P use state of the driver (S550). Then, it is determined whether the state of running continues (S560), and when the state of running continues (YES in S560), the above-described operations (S510 to S550) are repeated. Conversely, when the state of running has ended (NO in S560), the DRE system is terminated.

Figure 7:
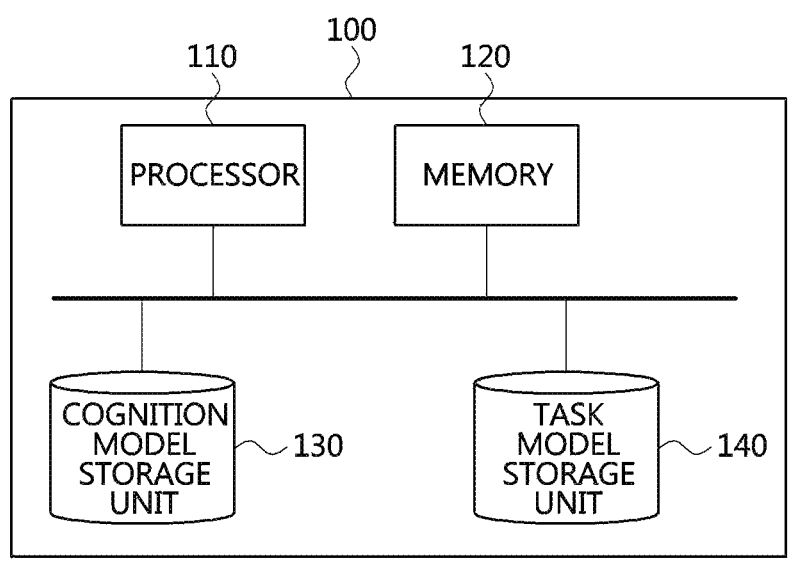
FIG. 7 is a block diagram illustrating a DRE apparatus according to another embodiment of the present invention.

FIG. 7 is a block diagram illustrating a DRE apparatus according to another embodiment of the present invention.

The DRE apparatus 100 according to the embodiment of the present invention may include a processor 110 and a memory 120 for storing at least one command executed through the processor 110.

Referring to FIG. 7, the DRE apparatus 100 may further include a cognition model storage unit 130 and a task model storage unit 140.

The cognition model storage unit 130 may be configured to store at least one cognition model including bodily sensory usage state information of a driver with respect to a behavior of the driver, that is, a usage level (a usage state) of a visual sense V, an auditory sense A, a cognitive sense C, and a psychomotor sense P.

The task model storage unit 140 may be configured to store at least one task model including information on bodily sensory usage distributions of at least one task candidate.

The at least one command includes a command for analyzing a bio-signal and a behavior of a driver through collected driver information, a command for determining a bodily sensory usage state of the driver from the behavior of the driver, a command for inferring a task by deriving chances of task candidates that are probable to occur from the driver during drive from the bodily sensory usage state of the driver, a command for determining the intention of the driver on the basis of the inferred chances of the task candidates, and a command for calculating driver readiness using the intention of the driver.

The bodily sensory usage state of the driver includes a visual sense V, an auditory sense A, a cognitive sense C, and a psychomotor sense P of the driver.

The chances of the task candidates include a posterior probability value for each task candidate calculated using at least one of a bodily sensory usage state of each of the task candidates and a situation awareness state of the driver.

The command for inferring a task may include a command for acquiring bodily sensory usage state information of at least one task candidate from a task model in which bodily sensory usage level information of at least one task is accumulated and stored and a command for calculating a global posterior probability for the task by using the bodily sensory usage state information of the at least one task candidate as a prior probability.

The command for determining the intention of the driver may include a command for determining an intention of the driver from the inferred task using an accumulated task inference history.

The command for calculating the driver readiness using the intention of the driver may include a command for calculating the driver readiness in consideration of at least one of the intention of the driver and a total workload of the driver.

The at least one command may further include a command for collecting bio-information of the driver and a command for identifying a health status of the driver by analyzing the bio-information of the driver.

Further, the DRE apparatus according to the present invention may operate in conjunction with at least one sensor for sensing driver information, vehicle information, and driving environment information and at least one user interaction device for maintaining the driver readiness at a reference value or higher. In this case, the DRE apparatus, the at least one sensor, and the at least one user interaction device may be integrated into a single system to constitute a system for assisting a driver according to an embodiment of the present invention.

The operations of the methods according to the embodiments may be embodied as computer-readable programs or codes on a computer-readable recording medium. The computer-readable recording medium is any data storage device that can store data that can be thereafter read by a computer system. In addition, the computer-readable recording medium may also be distributed over network-coupled computer systems so that the computer-readable program or code is stored and executed in a distributed fashion.

In addition, examples of the computer-readable recording medium may include a hardware device specially constructed to store and execute a program instruction, for example, a read-only memory (ROM), a random-access memory (RAM), and a flash memory. The program command may include a high-level language code executable by a computer through an interpreter in addition to a machine language code made by a compiler.

Some aspects of the present invention have been described in the context of the apparatus, but may represent description of a method corresponding thereto, and a block or an apparatus correspond to an operation of a method or a feature thereof. Similarly, some aspects having been described in the context of the method may also be represented by a block or items corresponding to the method or a feature of an apparatus corresponding to the method. Some or all of the operations of the method may be performed, for example, by a hardware device, such as a microprocessor, a programmable computer, or an electronic circuit (or using the hardware device). In some embodiments, one or more of most important operations of the method may be performed by such a device.

In some embodiments, a programmable logic device (for example, a field programmable gate array) may be used to perform some or all of the above described functions of the methods. In some embodiments, a field programmable gate array may operate together with a microprocessor to perform one of the above described methods. In an implementation, the methods may be performed by any hardware device.

As should be apparent from the above, the embodiments of the present invention can increase the safety of the automated vehicle by measuring the driver readiness of the driver in real time to switch from the automated driving mode into the manual driving mode.

The present invention can ensure safe driving even when the driver dozes or takes a short rest while passing through a point at which the automated vehicle is operable under automated driving.

Accordingly, the present invention can provide a driver situation customized automated driving system by determining the driver readiness in consideration of a driving route and a driving environment.

In addition, the present invention can maintain the driver readiness at a predetermined level or higher by detecting the driver readiness when the driver readiness falls to be lower than or equal to a threshold, and driving a user interaction device inside the vehicle to provide the driver with stimulus.

Further, the present invention can provide an effect of preventing dangerous driving by continuously monitoring the health status of the driver using a bio-signal sensing device installed inside the vehicle.

While the exemplary embodiments of the present invention have been described in detail, it should be understood that various substitutions, additions, and modifications are possible without departing from the scope and spirit of the present invention, and the scope of the present invention is limited by the claims and the equivalents thereof.

What is claimed is:

1. A method of estimating driver readiness in a vehicle supporting automated driving, the method comprising:
analyzing a bio-signal and a behavior of a driver through collected driver information;
determining a bodily sensory usage state of the driver from at least one of the bio-signal and the behavior of the driver;
deriving chances of task candidates that are probable to occur from the driver during driving from the bodily sensory usage state of the driver to infer a task;
determining an intention of the driver on the basis of the inferred chances of the task candidates; and
calculating driver readiness using the intention of the driver,
wherein the deriving of the chances of task candidates that are probable to occur during driving from the bodily sensory usage state of the driver includes:
acquiring bodily sensory usage state information of at least one task candidate from a task model in which bodily sensory usage level information of at least one task is accumulated and stored; and
calculating a global posterior probability of the task using the bodily sensory usage state of the at least one task candidate as a prior probability,
wherein the bio signal includes at least one of electroencephalogram (EEG), electrocardiogram (ECG), galvanic skin response (GSR), photoelectric pulse diagram (PPG), skin temperature (SKT), respiration rate.

2. The method of claim 1, wherein the bodily sensory usage state of the driver includes usage states of a visual sense (V), an auditory sense (A), a cognitive sense (C), and a psychomotor sense (P).

3. The method of claim 1, wherein the chances of the task candidates include a posterior probability value for each task candidate calculated using at least one of a bodily sensory usage state of each task candidate and a situation awareness state of the driver.

4. The method of claim 1, wherein the determining of the intention of the driver on the basis of the inferred chances of the task candidates includes determining the intention of the driver from a task inferred using an accumulated task inference history.

5. The method of claim 4, wherein the calculating of the driver readiness using the intention of the driver includes calculating the driver readiness by considering at least one of the intention of the driver and a total workload of the driver.

6. The method of claim 5, wherein the calculating of the driver readiness using the intention of the driver includes calculating the driver readiness by further considering a health status of the driver and reaction time information for take over request (TOR).

7. The method of claim 1, further comprising:
collecting bio-information of the driver; and
analyzing the bio-information of the driver to identify a health status of the driver.

8. An apparatus for estimating driver readiness in a vehicle supporting automated driving, the apparatus comprising:
a processor; and
a memory configured to store at least one command executed through the processor,
wherein the at least one command includes:
a command configured to analyze a bio-signal and a behavior of a driver through collected driver information;
a command configured to determine a bodily sensory usage state of the driver from at least one of the bio-signal and the behavior of the driver;

a command configured to infer a task by deriving chances of task candidates that are probable to occur from the driver during drive from the bodily sensory usage state of the driver;
a command configured to determine an intention of the driver on the basis of the inferred chances of the task candidates; and
a command configured to calculate driver readiness using the intention of the driver,
wherein the command configured to infer the task includes:
a command configured to acquire bodily sensory usage state information of at least one task candidate from a task model in which bodily sensory usage level information of at least one task is accumulated and stored; and
a command configured to calculate a global posterior probability for the task by using the bodily sensory usage state information of the at least one task candidate as a prior probability, and
wherein the bio signal includes at least one of electroencephalogram (EEG), electrocardiogram (ECG), galvanic skin response (GSR), photoelectric pulse diagram (PPG), skin temperature (SKT), respiration rate.

9. The apparatus of claim 8, wherein the bodily sensory usage state of the driver includes usage states of a visual sense (V), an auditory sense (A), a cognitive sense (C), and a psychomotor sense (P).

10. The apparatus of claim 8, further comprising a task model in which bodily sensory usage level information of at least one task is accumulated and stored.

11. The apparatus of claim 8, wherein the chances of the task candidates include a posterior probability value for each task candidate calculated using at least one of a bodily sensory usage state of each task candidate and a situation awareness state of the driver.

12. The apparatus of claim 8, wherein the command configured to determine the intention of the driver includes a command configured to determine the intention of the driver from a task inferred using an accumulated task inference history.

13. The apparatus of claim 12, wherein the command configured to calculate the driver readiness using the intention of the driver includes a command configured to calculate the driver readiness by considering at least one of the intention of the driver and a total workload of the driver.

14. The apparatus of claim 8, wherein the at least one command further includes:

a command configured to collect bio-information of the driver; and
a command configured to identify a health status of the driver by analyzing the bio-information of the driver.

15. A method of assisting a driver in a vehicle supporting automated driving, the method comprising:
deriving chances of task candidates that are probable to occur from the driver during driving from a bodily sensory usage state of the driver to infer a task;
calculating driver readiness on the basis of the chances of the task candidates;
determining whether the driver readiness is higher than or equal to a readiness threshold; and
operating at least one driver interaction device on the basis of the driver readiness in consideration of at least one of a driving environment, a driving route, vehicle information, and a health status of the driver,
wherein the deriving of the chances of task candidates that are probable to occur during driving from the bodily sensory usage state of the driver includes:
acquiring bodily sensory usage state information of at least one task candidate from a task model in which bodily sensory usage level information of at least one task is accumulated and stored; and
calculating a global posterior probability of the task using the bodily sensory usage state of the at least one task candidate as a prior probability, and
wherein the bio signal includes at least one of electroencephalogram (EEG), electrocardiogram (ECG), galvanic skin response (GSR), photoelectric pulse diagram (PPG), skin temperature (SKT), respiration rate.

16. The method of claim 15, wherein the bodily sensory usage state of the driver includes usage states of a visual sense (V), an auditory sense (A), a cognitive sense (C), and a psychomotor sense (P).

17. The method of claim 15, wherein the chances of the task candidates include a posterior probability value for each task candidate calculated using at least one of a bodily sensory usage state of each task candidate and a situation awareness state of the driver.

18. The method of claim 15, wherein the calculating of the driver readiness on the basis of the chances of the task candidates includes:
determining an intention of the driver from a task inferred using an accumulated task inference history; and
calculating the driver readiness by considering at least one of the intention of the driver and a total workload of the driver.

* * * * *